United States Patent [19]
von Deyn et al.

[11] Patent Number: 5,846,906
[45] Date of Patent: Dec. 8, 1998

[54] HERBICIDALLY ACTIVE PHENYLDIKETONE COMPOUNDS

[75] Inventors: Wolfgang von Deyn, Neustadt; Regina Luise Hill, Speyer; Uwe Kardorff, Mannheim; Stefan Engel, Idstein; Martina Otten, Ludwigshafen; Marcus Vossen, Mannheim; Peter Plath, Frankenthal; Harald Rang, Altrip; Albrecht Harreus, Ludwigshafen; Hartmann König, Heidelberg; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 875,659

[22] PCT Filed: Feb. 14, 1996

[86] PCT No.: PCT/EP96/00624

§ 371 Date: Jul. 30, 1997

§ 102(e) Date: Jul. 30, 1997

[87] PCT Pub. No.: WO96/26193

PCT Pub. Date: Aug. 29, 1996

[30] Foreign Application Priority Data

Feb. 24, 1995 [DE] Germany ............... 195 06 571.9

[51] Int. Cl.[6] .................. A01N 43/80; A01N 43/76; C07D 261/10; C07D 263/30; C07D 277/22; C07D 307/38; C07D 521/00
[52] U.S. Cl. .................. 504/221; 504/234; 504/242; 504/261; 504/263; 504/244; 504/265; 504/266; 504/270; 504/271; 504/274; 504/283; 504/288; 504/289; 504/290; 504/294; 504/295; 504/291; 504/309; 544/53; 544/318; 544/335; 546/174; 546/330; 548/128; 548/131; 548/136; 548/141; 548/143; 548/204; 548/214; 548/236; 548/247; 548/267.4; 548/550; 548/551; 548/370.1; 549/38; 549/39; 549/77; 549/450; 549/451; 558/405
[58] Field of Search .............. 558/405; 548/146, 548/215, 343.5, 343.1, 204, 214, 236, 247, 267.4, 550, 551, 370.1, 128, 131, 136, 141, 143; 504/221, 234, 242, 244, 261, 263, 265, 266, 269, 270, 271, 274, 283, 288, 289, 290, 291, 294, 295, 309; 544/53, 318, 335; 546/174, 330; 549/77, 38, 451, 39, 496

[56] References Cited

FOREIGN PATENT DOCUMENTS

| | | |
|---|---|---|
| 195 247 | 2/1989 | European Pat. Off. . |
| 0496630 | 7/1992 | European Pat. Off. . |
| 0496631 | 7/1992 | European Pat. Off. . |
| 0625505 | 11/1994 | European Pat. Off. . |
| 0625508 | 11/1994 | European Pat. Off. . |
| 95/25099 | 9/1995 | WIPO . |

*Primary Examiner*—Floyd D. Higel
*Attorney, Agent, or Firm*—Keil & Weinkauf

[57] ABSTRACT

Herbicidally active phenyldiketone compounds of the formula I

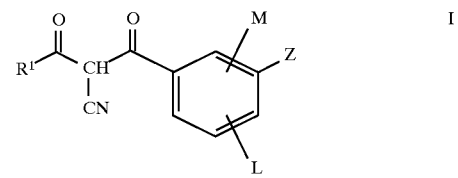

in which the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy, or halogen, cyano, nitro, a group —$(Y)_n$—$S(O)_m R^7$ or a group —$(Y)_n$—CO—$R^8$, Z is a 5- or 6-membered heterocyclic saturated or unsaturated radical which has one to three hetero atoms selected from the group consisting of oxygen, sulfur or nitrogen and which is unsubstituted or substituted by halogen, cyano, nitro, a group —CO—$R^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or which forms a bicyclic system with a substituted or unsubstituted phenyl ring, a fused carbocycle or a fused second heterocycle, Y is O or $NR^9$, n is zero or one, m is zero, one or two, $R^7$ is $C_1$–$C_4$-alkyl, $C_1$–$C_4$-haloalkyl or $NR^9 R^{10}$, $R^8$ is $C_1$–$C_4$-alkyl, $C_1$–$C_4$-haloalkyl, $C_1$–$C_4$-alkoxy or $NR^9 R^{10}$, $R^9$ is hydrogen or $C_1$–$C_4$-alkyl, $R^{10}$ is $C_1$–$C_4$-alkyl, $R^1$ is cyclopropyl, 1-methylcyclopropyl, 1-methylthiocyclopropyl or tert-butyl;

and agriculturally salts of the compounds I.

8 Claims, No Drawings

HERBICIDALLY ACTIVE PHENYLDIKETONE COMPOUNDS

This application is a 371 of PCT/EP96/00624 filed Feb. 14, 1996 published as WO96/26193 Aug. 29, 1996.

The present invention relates to novel phenyldiketone compounds which are herbicidally active, to processes for the preparation of the phenyldiketone compounds, to compositions comprising them, and to the use of these compounds or the compositions comprising them for controlling weeds.

The literature discloses herbicidally active phenyldiketone compounds, for example EP 625505.

However, the herbicidal properties of the known compounds and their tolerance by crop plants are only moderately satisfactory.

It was an object of the invention to find novel phenyldiketone derivatives which have improved properties.

We have found that this object is achieved by novel phenyldiketone compounds of the formula I

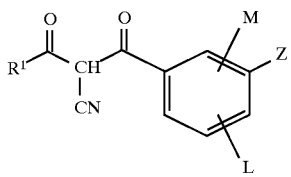

in which the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy, or halogen, cyano, nitro, a group —$(Y)_n$—S(O)$_m$R$^7$ or a group —$(Y)_n$—CO—R$^8$, Z is a 5- or 6-membered heterocyclic saturated or unsaturated radical which has one to three hetero atoms selected from the group consisting of oxygen, sulfur or nitrogen and which is unsubstituted or substituted by halogen, cyano, nitro, a group —CO—R$^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or phenyl which is unsubstituted or substituted by halogen, cyano, nitro, $C_1$–$C_4$-alkyl or $C_1$–$C_4$-haloalkyl or an oxo group which may also exist as a hydroxyl group in the tautomeric form, or which forms a bicyclic system with a fused phenyl ring which is unsubstituted or substituted by halogen, cyano, nitro, $C_1$–$C_4$-alkyl or $C_1$–$C_4$-haloalkyl, a fused carbocycle or a fused, second heterocycle which is unsubstituted or substituted by halogen, cyano, nitro, $C_1$–$C_4$-alkyl, di-$C_1$–$C_4$-alkylamino, $C_1$–$C_6$-alkoxy, $C_1$–$C_4$-haloalkoxy or $C_1$–$C_4$-haloalkyl, Y is O or NR$^9$, n is zero or one, m is zero, one or two, R$^7$ is $C_1$–$C_4$-alkyl, $C_1$–$C_4$-haloalkyl or NR$^9$R$^{10}$, R$^8$ is $C_1$–$C_4$-alkyl, $C_1$–$C_4$-haloalkyl, $C_1$–$C_4$-alkoxy or NR$^9$R$^{10}$, R$^9$ is hydrogen or $C_1$–$C_4$-alkyl, R$^{10}$ is $C_1$–$C_4$-alkyl, R$^1$ is cyclopropyl, 1-methylcyclopropyl, 1-methylthiocyclopropyl or tert-butyl;

and by agriculturally customary salts of the compounds I.

The phenyldiketone derivatives can exist in the following tautomeric forms:

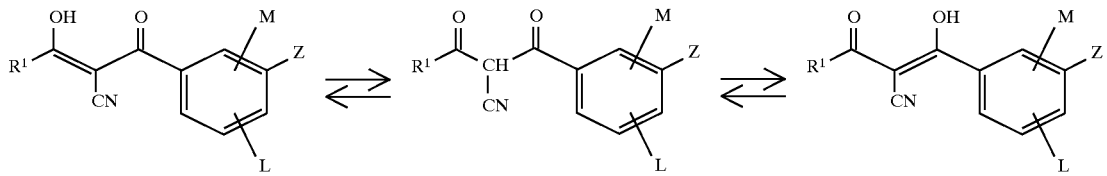

Compounds of the formula I are obtained by acylating the magnesium enolate A2 of a cyanoketone of the formula A1

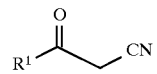

with a benzoic acid derivative of the formula III (T=Cl) to give the enolized compound Ic.

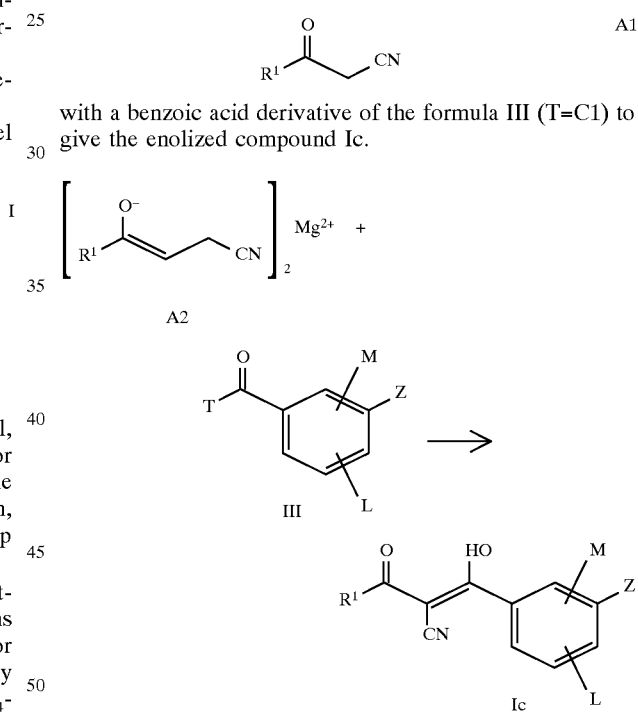

In the abovementioned formulae, L, M and Z have the meanings mentioned at the outset, and T is halogen.

The first step of the reaction sequence is carried out in such a way that a methanolic solution of a cyanoketone of the formula A1 is treated with magnesium and a small amount of $CCl_4$, and this is allowed to react until the magnesium enolate is obtained. Analogous C-acylations of cyanoketones are described, for example, in EP-A 496 630 and EP-A 496 631.

After the methanol has been removed, the magnesium enolate obtained, of the formula A2, is dissolved in toluene or acetonitrile, acetonitrile being preferred, and then an amount of the acid chloride of the formula III which is equivalent to A1 is added dropwise in the form of a solution in acetonitrile. After the mixture has been stirred at 25° C.

to 50° C. for 1–16 hours, the reaction is complete. For working-up, the mixture is concentrated in vacuo, the residue which remains is taken up in a solvent, such as ethyl acetate or methylene chloride, and washed using 10 percent strength HCl in order to destroy the magnesium salt. After the organic phase has been washed with water, it is dried using a desiccant, such as sodium sulfate, and concentrated. The product is precipitated from the residue which remains by trituration with a hydrocarbon, such as petroleum ether, cyclohexane or n-pentane.

The cyanoketones of the formula A1 which are used as starting materials are generally known compounds. They can be obtained, for example, by reacting cyanoacetic acid with butyllithium and subsequently with an acid chloride $R^1$—COCl.

The acid chlorides $R^1$—COCl are obtained in a manner known per se from the corresponding carboxylic acids $R^1$—COOH by reacting them with thionyl chloride. The carboxylic acids $R^1$—COOH are known from the literature; pivalic acid and cyclopropanecarboxylic acid are commercially available compounds. 1-Methylcyclopropanecarboxylic acid is obtained either by hydrolyzing the commercially available ethyl ester or, in a manner known per se, by methylating the lithium α-lithiocyclopropanecarboxylate [Warner+Le, JOC 47, 893 (1982)]. 1-Methylthiocyclopropanecarboxylic acid is obtained from 1-methylthiocyclopropanecarbonitrile in a manner known per se, and this, in turn, can be prepared from methylmercaptoacetonitrile and ethylene dibromide in the presence of sodium amide [German Laid-Open Application DOS 21 20 908=CA 76: 72099].

Benzoic acid derivatives of the formula III can be prepared as follows:

Benzoyl halides such as, for example, benzoyl chlorides of the formula III (T=Cl) are prepared in a manner known per se by reacting the benzoic acids of the formula III (T=OH) with thionyl chloride.

The benzoic acids of the formula III (T=OH) can be prepared in a manner known per se from the corresponding esters of the formula III (T=$C_1$–$C_4$-alkoxy) by means of acidic or alkaline hydrolysis.

The intermediates of the formula III can be synthesized for example in accordance with equations 2 and 3 via the routes described hereinbelow.

Equation 2

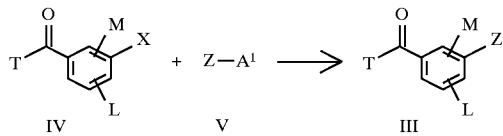

T is $C_1$–$C_4$-alkoxy,
X is Cl, Br, I, —OS(O)$_2$CF$_3$, —OS(O)$_2$F,
$A^1$ is Sn($C_1$–$C_4$-Alkyl)$_3$, B(OH)$_2$, ZnHal, Hal being Cl or Br, and
L, M and Z are as defined above.

Thereupon, the arylhalogen compounds or arylsulfonates IV can be reacted in a manner known per se with heteroaryl stannates (Stille couplings), heteroaryl-boron compounds (Suzuki couplings) or heteroaryl-zinc compounds (Negishi reaction) V (cf., for example, Synthesis 1987, 51–53, Synthesis 1992, 413) in the presence of a palladium or nickel transition metal catalyst and in the presence or absence of a base to give the novel compounds of the general formula IIIb.

The benzoic acid derivatives of the formula III can also be obtained by reacting corresponding bromine- or iodine-substituted compounds of the formula VI Equation 3

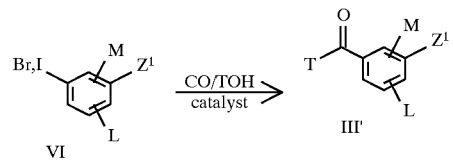

where
$Z^1$ is Z or CN,
T is OH or $C_1$–$C_4$-alkoxy and
L and M have the abovementioned meanings, with carbon monoxide and water under elevated pressure in the presence of a palladium, nickel, cobalt or rhodium transition metal catalyst and of a base.

Preferred phenyldiketone derivatives for the purposes of the present invention are those of the formula Ia

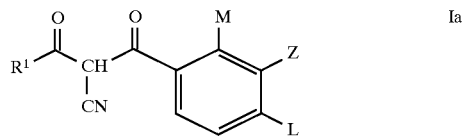

where
L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano,
M is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and
$R^1$ and Z are as defined above.

Other preferred phenyldiketone derivatives are those of the formula Ib

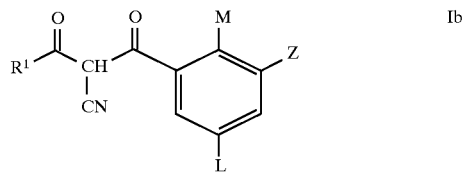

where
L and M are $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and
$R^1$ and Z are as defined above.

The catalysts nickel, cobalt, rhodium and, in particular, palladium can be present in the form of metals or in the form of customary salts, such as in the form of halogen compounds, eg. PdCl$_2$, RhCl$_3$·H$_2$O, acetates, eg. Pd(OAc)$_2$, cyanides and the like, at the known valency levels. There may furthermore exist metal complexes with tertiary phosphines, metal alkylcarbonyls, metal carbonyls, eg. CO$_2$(CO)$_8$, Ni(CO)$_4$, metal carbonyl complexes with tertiary phosphines, eg. (PPh$_3$)$_2$Ni(CO)$_2$, or transition metal salts complexed with tertiary phosphines. The last-mentioned embodiment is particularly preferred in the case of palladium as the catalyst. The type of phosphine ligand may be varied within a wide range. For example, they may be represented by the following formulae:

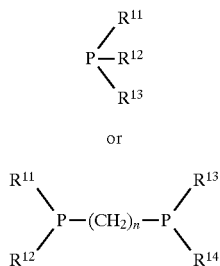

or $$R^{11} \diagdown P-(CH_2)_n-P \diagup R^{13}$$
$$R^{12} \diagup \qquad \diagdown R^{14}$$

where n denotes the numbers 1, 2, 3 or 4 and the radicals $R^{11}$ to $R^{14}$ are low-molecular-weight alkyl, eg. $C_1$–$C_6$-alkyl, aryl, $C_1$–$C_4$-alkylaryl, eg. benzyl, phenethyl or aryloxy. Aryl is, for example, naphthyl, anthryl and, preferably, substituted or unsubstituted phenyl. As regards the substituents, care must merely be taken that they are inert in the carboxylation reaction, otherwise they can be varied within a wide range and include all inert C-organic radicals, such as $C_1$–$C_6$-alkyl radicals, eg. methyl, carboxyl radicals, such as COOH, COOM (M is, for example, an alkali metal, alkaline earth metal or ammonium salt), or C-organic radicals which are bonded via oxygen, such as $C_1$–$C_6$-alkoxy radicals.

The phosphine complexes can be prepared in a manner known per se, for example as described in the documents mentioned at the outset. For example, customary, commercially available metal salts, such as $PdCl_2$ or $Pd(OCOCH_3)_2$ are used as starting materials, and the phosphine, eg. $P(C_6H_5)_3$, $P(n-C_4H_9)_3$, $PCH_3(C_6H_5)_2$, 1,2-bis(diphenylphosphino)ethane, is added.

The amount of phosphine based on the transition metal is usually 0 to 20, in particular 0.1 to 10, mol equivalents, particularly preferably 1 to 5 mol equivalents.

The amount of transition metal is not critical. For cost reasons, preferably a small amount, for example from 0.1 to 10 mol %, in particular 1 to 5 mol %, based on the starting material VI, will naturally be used.

To prepare the benzoic acids III (T=OH), the reaction is carried out with carbon monoxide and at least equimolar amounts of water, based on the starting materials VI. The reactant water can simultaneously also react as the solvent, i.e. the maximum amount is not critical.

Alternatively, it may be advantageous to use, as the solvent, an inert solvent other than the reactant, or the base used for the carboxylation reaction, depending on the nature of the starting materials and the catalysts used.

Suitable inert solvents are solvents which are customary for carboxylation reactions, such as hydrocarbons, eg. toluene, xylene, hexane, pentane, cyclohexane, ethers, eg. methyl tert-butyl ether, tetrahydrofuran, dioxane, dimethoxyethane, substituted amides, such as dimethylformamide, persubstituted ureas, such as tetra-$C_1$–$C_4$-alkylureas, or nitriles, such as benzonitrile or acetonitrile.

In a preferred embodiment of the process, one of the reactants, in particular the base, is used in excess, thus dispensing with an additional solvent.

Bases which are suitable for the process are all inert bases which are capable of binding the hydrogen iodide or hydrogen bromide which is liberated during the reaction. Examples which may be mentioned are tertiary amines, such as tert-alkylamines, eg. trialkylamines, such as triethylamine, cyclic amines, such as N-methylpiperidine or N,N'-dimethylpiperazine, pyridine, alkali metal carbonates or alkali metal hydrogen carbonates, or tetraalkyl-substituted urea derivatives, such as tetra-$C_1$–$C_4$-alkylurea, eg. tetramethylurea.

The amount of base is not critical, 1 to 10, in particular 1 to 5, mol usually being used. If the base is simultaneously used as the solvent, such an amount will generally be chosen that the reactants are dissolved. For reasons of practicality, unnecessarily high excesses are avoided to save on costs, to be able to use small reaction vessels and to guarantee maximum contact between the reactants.

During the reaction, the carbon monoxide pressure is adjusted in such a way that there is always an excess of CO, based on VI. The carbon monoxide pressure is preferably 1 to 250 bar, in particular 5 to 150 bar, of CO at room temperature.

As a rule, the carbonylation reaction is carried out at from 20° to 250° C., in particular at 30° to 150° C., either continuously or batchwise. If the process is carried out batchwise, it is expedient to continuously inject carbon monoxide onto the reaction mixture in order to maintain a constant pressure.

Those arylhalogen compounds VI which are used as starting compounds and which are not already known can be prepared readily by a suitable combination of known syntheses.

For example, the halogen compounds VI can be obtained from corresponding anilines by Sandmeyer reaction, and these, in turn, can be synthesized by reducing suitable nitro compounds (cf., for example, for VI where $Z^1$=CN: Liebigs Ann. Chem. 1980, 768–778). The aryl bromides VI can additionally be obtained by directly brominating suitable starting compounds [cf., for example, Monatsh. Chem. 99, 815–822 (1968)].

Equation 4

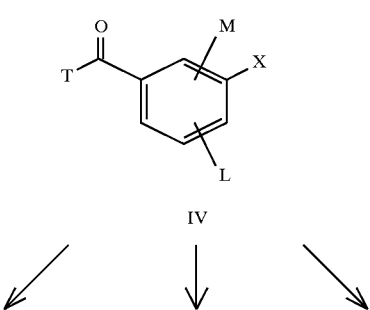

IV

-continued
Equation 4

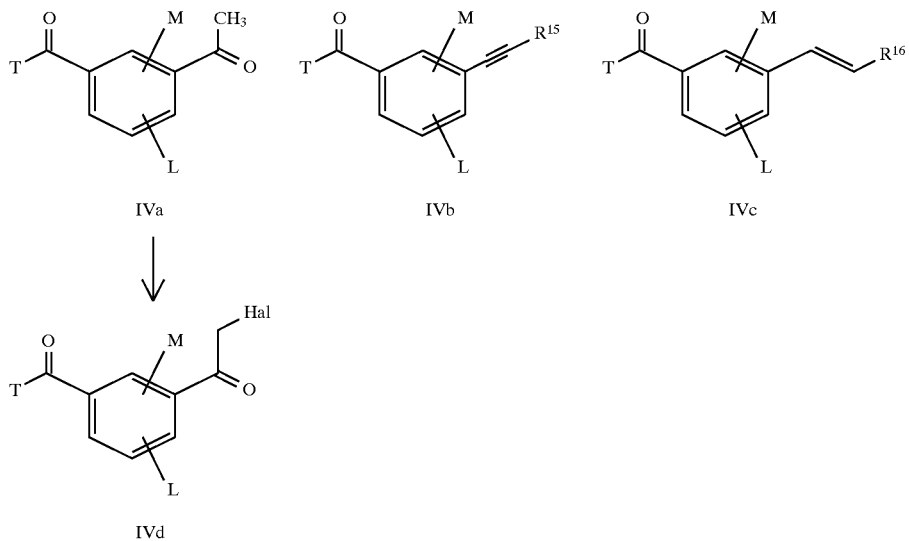

T is $C_1$–$C_4$-alkoxy,

X is Cl, Br, I, —OS(O)$_2$CF$_3$, —OS(O)$_2$F,

L, M and Z are as defined above, $R^{15}$ is hydrogen, $C_1$–$C_4$-alkyl, $C_1$–$C_4$-haloalkyl, $C_3$–$C_8$-cycloalkyl, substituted or unsubstituted phenyl or trimethylsilyl, $R^{16}$ is hydrogen, $C_1$–$C_4$-haloalkyl, $C_3$–$C_8$-cycloalkyl or substituted or unsubstituted phenyl.

Starting from the arylhalogen compounds or arylsulfonates IV, aryl methyl ketones IVa can be prepared by processes known from the literature in the presence of a palladium or nickel transition metal catalyst and in the presence or absence of a base by means of reaction with vinyl alkyl ethers, followed by hydrolysis [cf., for example, Tetrahedron Lett. 32, 1753–1756 (1991)].

The ethynylated aromatics IVb can be prepared in a manner known per se by reacting arylhalogen compounds or arylsulfonates IV with substituted acetylenes in the presence of a palladium or nickel transition metal catalyst (for example Heterocycles, 24, 31–32 (1986)). Derivatives IVb where $R^{15}$=H are expediently obtained from the silyl compounds IVb, $R^{16}$=—Si(CH$_3$)$_3$ [J. Org. Chem. 46, 2280–2286 (1981)].

The arylalkenes IVc are obtained by Heck reaction of arylhalogen compounds or arylsulfonates IV with olefins in the presence of a palladium catalyst (cf., for example, Heck, Palladium Reagents in Organic Synthesis, Academic Press, London 1985, or Synthesis 1993, 735–762).

Those benzoyl derivatives IV which are used as starting compounds and which are not already known [cf., for example, Coll. Czech. Chem. Commn. 40, 3009–3019 (1975)] can be prepared readily by a suitable combination of known syntheses.

For example, the sulfonates IV (X=—OS(O)$_2$CF$_3$, —OS(O)$_2$F) can be obtained from the corresponding phenols. Those phenols, in turn, which are not already known (cf., for example, EP 195247) can be prepared by known methods (cf., for example, Synthesis 1993, 735–762).

The halogen compounds IV (X=Cl, Br or I) can be prepared from corresponding anilines by Sandmeyer reaction.

Equation 5

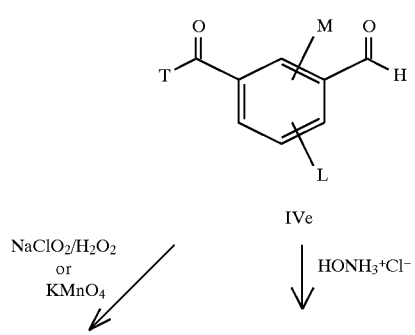

IVe

NaClO$_2$/H$_2$O$_2$
or
KMnO$_4$

HONH$_3^+$Cl$^-$

-continued
Equation 5

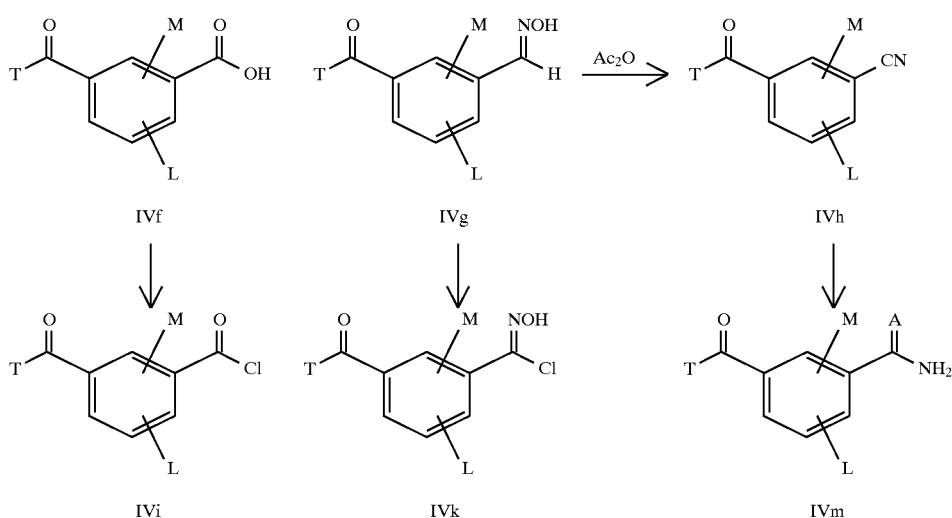

A is S, NH or NOH,

T is $C_1$–$C_4$-alkoxy and

L and M are as defined above.

Isophthalic acid derivatives IVf can be prepared from the aldehydes IVe by known methods [see J. March Advanced Organic Chemistry, 3rd Ed., p. 629 et seq., Wiley-Interscience Publication (1985)].

The oximes IVg are advantageously obtained by reacting aldehydes IVe with hydroxylamine in a manner known per se (see J. March Advanced Organic Chemistry, 3rd Ed., p. 805–806, Wiley-Interscience Publication (1985)].

The oximes IVg can be converted into nitrites IVh by methods which are known per se [see J. March Advanced Organic Chemistry, 3rd Ed., p. 931–932, Wiley-Interscience Publication (1985)].

Those aldehydes IVe which are required as starting compounds and which are not already known can be prepared by known methods. For example, they can be synthesized from the methyl compounds VII in accordance with equation 6.

Equation 6

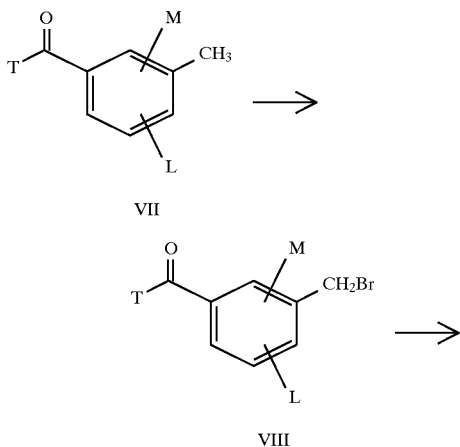

-continued
Equation 6

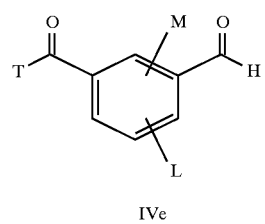

The radicals T, M and L have the meanings given under equation 5. The methyl compounds VII can be reacted to the benzyl bromides VIII by generally known methods, for example with N-bromosuccinimide or 1,3-dibromo-5,5-dimethylhydantoin. The reaction of benzyl bromides to benzaldehydes IVe is equally known from the literature [cf. Synth. Commun. 22 1967–1971 (1992)].

The precursors IVa to IVh are suitable for the synthesis of heterocyclic intermediates III.

For example, 5-oxazolyl derivatives [cf., for example, J. Heterocyclic Chem., 28, 17–28 (1991)] or 4-thiazolyl derivatives [cf., for example, Metzger, Thiazoles in: The Chemistry of heterocyclic compounds, Vol. 34, p. 175 et seq. (1976)] from the acetophenones IVa via the halogenated intermediate IVd.

The acetylenes IVb, or the alkenes IVc, are suitable for the synthesis of 4-isoxazolyl, 5-isoxazolyl, 4,5-dihydroisoxazol-4-yl, 4,5-dihydroisoxazol-5-yl derivatives [cf., for example, Houben-Weyl, Methoden der organischen Chemie [Methods in Organic Chemistry], 4th Ed., Vol. X/3, p. 843 et seq. (1965)].

Using, for example, processes known from the literature, it is possible to prepare 2-oxazolyl, 1,2,4-oxadiazol-5-yl and 1,3,4-oxadiazol-2-yl derivatives [cf., for example, J. Heterocyclic Chem., 28, 17–28 (1991)] or 2-pyrrolyl derivatives [cf., for example, Heterocycles 26, 3141–3151 (1987)] from the benzoic acids IVf or from the acid chlorides IVi which can be obtained therefrom by standard methods.

1,2,4-Triazol-3-yl derivatives can be synthesized from benzonitriles IVh by known methods [cf., for example, J. Chem. Soc. 3461–3464 (1954)].

The benzonitriles IVh can be converted into 1,2,4-oxadiazol-3-yl [cf., for example, J. Heterocyclic Chem., 28, 17–28 (1991)] 2-thiazolyl, 4,5-dihydrothiazol-2-yl or 5,6-dihydro-4H-1,3-thiazin-2-yl derivatives [cf., for example, Houben-Weyl, Methoden der organischen Chemie [Methods in Organic Chemistry], 4th Ed., Vol. E5, p. 1268 et seq. (1985)] via the intermediate of the thioamides, amide oximes or amidines IVm. Processes known from the literature may also be used for obtaining, from the thioamides IVm (A=S), 1,2,4-thiadiazol-5-yl derivatives [cf., for example, J. Org. Chem. 45, 3750–3753 (1980)] or 1,3,4-thiadiazol-2-yl derivatives [cf., for example, J. Chem. Soc., Perkin Trans. I, 1987–1991 (1982)].

The oximes IVg can be converted into 3-isoxazolyl derivatives in a manner known per se via the intermediate of the hydroxamoyl chlorides IVk [cf., for example, Houben-Weyl, Methoden der organischen Chemie [Methods in Organic Chemistry], 4th Ed., Vol. X/3, p. 843 et seq. (1965)].

Taking into consideration the intended use of the benzoyl derivatives of the general formula I, the following radicals are suitable as substituents:

L and M are hydrogen, $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl or 1-ethyl-2-methyl-propyl, in particular methyl, ethyl, 1-methylethyl, 1-methylpropyl, 2-methylpropyl, 1,1-dimethylethyl and 1,1-dimethylpropyl;

$C_2$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 3-methyl-2-butenyl, 1-methyl-2-butenyl, 2-methyl-2-butenyl, 1-methyl-3-butenyl, 2-methyl-4-butenyl, 3-methyl-3-butenyl, 1,1-dimethyl-2-propenyl,1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3 butenyl, 2-ethyl-2-butenyl, 2-ethyl-3-butenyl, 1,1,2-trimethyl-2-propenyl, 1-ethyl-1-methyl-2-propenyl and ethyl-2-methyl-2-propenyl, in particular 1-methyl-2-propenyl, 1-methyl-2-butenyl, 1,1-dimethyl-2-propenyl and 1,1-dimethyl-2-butenyl;

$C_2$–$C_6$-alkynyl, such as propargyl, 2-butynyl, 3-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

$C_1$–$C_4$-alkoxy, such as methoxy, ethoxy, n-propoxy, 1-methylethoxy, n-butoxy, 1-methylpropoxy, 2-methylpropoxy and 1,1-dimethylethoxy, in particular $C_1$–$C_3$-alkoxy, such as methoxy, ethoxy, i-propoxy, it being possible for these groups to be unsubstituted or substituted by one to five halogen atoms, such as fluorine, chlorine, bromine and iodine, preferably fluorine and chlorine, or $C_1$–$C_4$-alkoxy as mentioned above.

The above-defined group —$(Y)_n$—$S(O)_m R^7$ is, for example, $C_1$–$C_4$-alkylthio, such as methylthio, ethylthio, n-propylthio, 1-methylethylthio, n-butylthio, 1-methylpropylthio, 2-methylpropylthio and 1,1-dimethylethylthio, in particular methylthio;

$C_1$–$C_4$-alkylsulfinyl, such as methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl, in particular methylsulfinyl;

$C_1$–$C_4$-alkylsulfonyl, such as methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, in particular methylsulfonyl;

$C_1$–$C_4$-alkoxysulfonyl, such as methoxysulfonyl, ethoxysulfonyl, n-propoxysulfonyl, 1-methylethoxysulfonyl, n-butoxysulfonyl, 1-methylpropoxysulfonyl, 2-methylpropoxysulfonyl and 1,1-dimethylethoxysulfonyl, in particular methoxysulfonyl;

N-$C_1$–$C_4$-alkylsulfamoyl, such as N-methylsulfamoyl, N-ethylsulfamoyl, N-n-propylsulfamoyl, N-1-methylethylsulfamoyl, N-n-butylsulfamoyl, N-1-methylpropylsulfamoyl, N-2-methylpropylsulfamoyl and N-1,1-dimethylethylsulfamoyl, in particular N-methylsulfamoyl;

N-$C_1$–$C_4$-alkylsulfinamoyl, such as N-methylsulfinamoyl, N-ethylsulfinamoyl, N-n-propylsulfinamoyl, N-1-methylethylsulfinamoyl, N-n-butylsulfinamoyl, N-1-methylpropylsulfinamoyl, N-2-methylpropylsulfinamoyl and N-1,1-dimethylethylsulfinamoyl, in particular N-methylsulfinamoyl;

di-$C_1$–$C_4$-alkylsulfamoyl, such as dimethylsulfamoyl, diethylsulfamoyl, dipropylsulfamoyl, dibutylsulfamoyl, N-methyl-N-ethylsulfamoyl, N-methyl-N-propylsulfamoyl, N-methyl-N-1-methylethylsulfamoyl, N-methyl-N-1,1-dimethylethylsulfamoyl, di-1-methylethylsulfamoyl, N-ethyl-N-1-methylethylsulfamoyl and N-ethyl-N-1,1-dimethylethylsulfamoyl, in particular dimethylsulfamoyl;

di-$C_1$–$C_4$-alkylsulfinamoyl, such as dimethylsulfinamoyl, diethylsulfinamoyl, dipropylsulfinamoyl, dibutylsulfinamoyl, N-methyl-N-ethylsulfinamoyl, N-methyl-N-propylsulfinamoyl, N-methyl-N-1-methylethylsulfinamoyl, N-methyl-N-1,1-dimethylethylsulfinamoyl, di-1-methylethylsulfinamoyl, N-ethyl-N-1-methylethylsulfinamoyl and N-ethyl-N-1,1-dimethylethylsulfinamoyl, in particular dimethylsulfinamoyl, $C_1$–$C_4$-alkylsulfinyloxy, such as methylsulfinyloxy, ethylsulfinyloxy, n-propylsulfinyloxy, 1-methylethylsulfinyloxy, n-butylsulfinyloxy, 1-methylpropylsulfinyloxy, 2-methylpropylsulfinyloxy and 1,1-dimethylethylsulfinyloxy, in particular methylsulfinyloxy;

$C_1$–$C_4$-alkylsulfonyloxy, such as methylsulfonyloxy, ethylsulfonyloxy, n-propylsulfonyloxy, 1-methylethylsulfonyloxy, n-butylsulfonyloxy, 1-methylpropylsulfonyloxy, 2-methylpropylsulfonyloxy and 1,1-dimethylethylsulfonyloxy, in particular methylsulfonyloxy;

$C_1$–$C_4$-alkylsulfinylamino, such as methylsulfinylamino, ethylsulfinylamino, n-propylsulfinylamino, 1-methylethylsulfinylamino, n-butylsulfinylamino, 1-methylpropylsulfinylamino, 2-methylpropylsulfinylamino and 1,1-dimethylethylsulfinylamino, in particular methylsulfinylamino;

$C_1$–$C_4$-alkylsulfonylamino, such as methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino, in particular methylsulfonylamino;

N-$C_1$–$C_4$-alkylsulfinyl-N-methylamino, such as N-methylsulfinyl-N-methylamino, N-ethylsulfinyl-N-methylamino, N-n-propylsulfinyl-N-methylamino, N-1-methylethylsulfinyl-N-methylamino, N-n-butylsulfinyl-N-methylamino, N-1-methylpropylsulfinyl-N-methylamino, N-2-methylpropylsulfinyl-N-methylamino and N-1,1-dimethylethylsulfinyl-N-methylamino, in particular N-methylsulfinyl-N-methylamino;

N-$C_1$–$C_4$-alkylsulfinyl-N-ethylamino, such as N-methylsulfinyl-N-ethylamino, N-ethylsulfinyl-N-ethylamino, N-n-propylsulfinyl-N-ethylamino, N-1-methylethylsulfinyl-N-ethylamino, N-n-butylsulfinyl-N-ethylamino, N-1-methylpropylsulfinyl-N-ethylamino, N-2-methylpropylsulfinyl-N-ethylamino and N-1,1-dimethylethylsulfinyl-N-ethylamino, in particular N-methylsulfinyl-N-ethylamino;

N-$C_1$–$C_4$-alkylsulfonyl-N-methylamino, such as N-methylsulfonyl-N-methylamino, N-ethylsulfonyl-N-methylamino, N-n-propylsulfonyl-N-methylamino, N-1-methylethylsulfonyl-N-methylamino, N-n-butylsulfonyl-N-methylamino, N-1-methylpropylsulfonyl-N-methyl-amino, N-2-methylpropylsulfonyl-N-methylamino and N-1,1-dimethylethylsulfonyl-N-methylamino, in particular N-methylsulfonyl-N-methylamino;

N-$C_1$–$C_4$-alkylsulfonyl-N-ethylamino, such as N-methylsulfonyl-N-ethylamino, N-ethylsulfonyl-N-ethylamino, N-n-propylsulfonyl-N-ethylamino, N-1-methylethylsulfonyl-N-ethylamino, N-n-butylsulfonyl-N-ethylamino, N-1-methylpropylsulfonyl-N-ethylamino, N-2-methylpropylsulfonyl-N-ethylamino and N-1,1-dimethylethylsulfonyl-N-ethylamino, in particular N-methylsulfonyl-N-ethylamino;

$C_1$–$C_4$-haloalkylthio, such as chloromethylthio, dichloromethylthio, trichloromethylthio, fluoromethylthio, difluoromethylthio, trifluoromethylthio, chlorofluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, in particular trifluoromethylthio.

The above-defined group —$(Y)_n$—CO—$R^8$ is, for example, $C_1$–$C_4$-alkylcarbonyl, such as methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, in particular methylcarbonyl;

$C_1$–$C_4$-alkoxycarbonyl, such as methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl and 1,1-dimethylethoxycarbonyl, in particular methoxycarbonyl;

N-$C_1$–$C_4$-alkylcarbamoyl, such as N-methylcarbamoyl, N-ethylcarbamoyl, N-n-propylcarbamoyl, N-1-methylethylcarbamoyl, N-n-butylcarbamoyl, N-1-methylpropylcarbamoyl, N-2-methylpropylcarbamoyl and N-1,1-dimethylethylcarbamoyl, in particular N-methylcarbamoyl;

di-$C_1$–$C_4$-alkylcarbamoyl, such as dimethylcarbamoyl, diethylcarbamoyl, dipropylcarbamoyl, dibutylcarbamoyl, N-methyl-N-ethylcarbamoyl, N-methyl-N-propylcarbamoyl, N-methyl-N-1-methylethylcarbamoyl, N-methyl-N-1,1-dimethylethylcarbamoyl, di-1-methylethylcarbamoyl, N-ethyl-N-1-methylethylcarbamoyl and N-ethyl-N-1,1-dimethylethylcarbamoyl, in particular dimethylcarbamoyl;

$C_1$–$C_4$-alkylcarbonyloxy, such as methylcarbonyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy and 1,1-dimethylethylcarbonyloxy, in particular methylcarbonyloxy;

$C_1$–$C_4$-alkylcarbonylamino, such as methylcarbonylamino, ethylcarbonylamino, n-propylcarbonylamino, 1-methylethylcarbonylamino, n-butylcarbonylamino, 1-methylpropylcarbonylamino, 2-methylpropylcarbonylamino and 1,1-dimethylethylcarbonylamino, in particular methylcarbonylamino;

N-$C_1$–$C_4$-alkylcarbonyl-N-methylamino, such as N-methylcarbonyl-N-methylamino, N-ethylcarbonyl-N-methylamino, N-n-propylcarbonyl-N-methylamino, N-1-methylethylcarbonyl-N-methylamino, N-n-butylcarbonyl-N-methylamino, N-1-methylpropylcarbonyl-N-methylamino, N-2-methylpropylcarbonyl-N-methylamino and N-1,1-dimethylethylcarbonyl-N-methylamino, in particular N-methylcarbonyl-N-methylamino.

Z is, for example, a 5- or 6-membered heterocyclic, saturated or unsaturated radical having one to three hetero atoms selected from the group consisting of oxygen, sulfur or nitrogen, for example a five-membered heteroaromatic ring such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl, 1,2,4-triazol-3-yl, 1,3,4-triazol-2-yl, 1,2,3-triazol-4-yl, 1,2,3-triazol-5-yl, 1,2,4-triazol-5-yl, tetrazol-5-yl, in particular 2-thiazolyl and 3-isoxazolyl;

a six-membered heteroaromatic ring such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-5-yl and 1,2,4-triazin-3-yl, 1,2,4-triazin-6-yl, 1,2,4,5-tetrazin-3-yl;

a 5- or 6-membered, saturated or partially unsaturated heterocycle having one to three nitrogen atoms and/or one or two oxygen or sulfur atoms, such as 2-tetrahydrofuranyl, 3-tetrahydrofuranyl, 2-tetrahydrothienyl, 3-tetrahydrothienyl, tetrahydrothiopyran-2-yl, tetrahydrothiopyran-3-yl, tetrahydrothiopyran-4-yl, 1,3-dithiolan-2-yl, 1,3-dithiolan-4-yl, 1-3-dithian-2-yl, 1,3-dithian-4-yl, 5,6-dihydro-4H-1,3-thiazin-2-yl, 1,3-oxathiolan-2-yl, 1,3-oxathian-2-yl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 1,3-dioxolan-2-yl, 1,3-dioxolan-4-yl, 1,3-dioxan-5-yl, 1,4-dioxan-2-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl, in particular 2-tetrahydrofuranyl, 1,3-dioxolan-2-yl and 1,3-dioxan-2-yl, which is unsubstituted or substituted by halogen as mentioned above, in particular fluorine or chlorine, cyano, nitro, a group —COR⁸, for example alkylcarbonyl as mentioned above, alkoxycarbonyl as mentioned above, N-alkylcarbamoyl as mentioned above and dialkylcarbamoyl as mentioned above;

$C_1$–$C_4$-alkyl as mentioned above, $C_1$–$C_4$-haloalkyl such as, for example, chloromethyl, difluoromethyl, dichloromethyl, trifluoromethyl, trichloromethyl, chlorodifluoromethyl, 1-fluoroethyl, 2-fluoroethyl, 2,2-difluoroethyl, 1,1,2,2-tetrafluoroethyl, 2,2,2-trifluoroethyl, 2-chloro-1,1,2-trifluoroethyl and pentafluoroethyl, decafluorobutyl, 1,1-bistrifluoromethyl-2,2,2-trifluoroethyl, preferably difluoromethyl, trifluoromethyl, trichloromethyl and chlorodifluoromethyl;

$C_3$–$C_8$-cycloalkyl such as, for example, cyclopropyl, cyclobutyl, cyclopentyl, cyclohexyl, cycloheptyl, cyclooctyl, in particular cyclopropyl and cyclohexyl;

$C_1$–$C_4$-alkoxy as mentioned above, $C_1$–$C_4$-haloalkoxy such as, for example, chloromethoxy, dichloromethoxy, trichloromethoxy, fluoromethoxy, difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular $C_1$–$C_3$-haloalkoxy, such as 2,2,2-trifluoroethoxy and 2-chloro-2,2-difluoroethoxy;

$C_1$–$C_4$-alkylthio as mentioned above, $C_1$–$C_4$-haloalkylthio as mentioned above, di-$C_1$–$C_4$-alkylamino such as, for example, dimethylamino, diethylamino, dipropylamino, dibutylamino, N-methyl-N-ethylamino, N-methyl-N-propylamino, N-methyl-N-1-methylethylamino, N-methyl-N-1,1-dimethylethylamino, di-1-methylethylamino, N-ethyl-N-1-methylethylamino and N-ethyl-N-1,1-dimethylethylamino;

unsubstituted or substituted phenyl or an oxo group which may also exist in the tautomeric form as a hydroxyl group, for example thiazolin-4,5-dion-2-yl, 3-oxo-3H-1,2,4-dithiazolyl or 2-oxo-2H-1,3,4-dithiazolyl.

Benzo-fused 5- or 6-membered heteroaromatic rings are, for example, benzofuranyl, benzothienyl, indolyl, benzoxazolyl, benzisoxazolyl, benzothiazolyl, benzisothiazolyl, benzopyrazolyl, indazolyl, 1,2,3-benzothiadiazolyl, 2,1,3-benzothiadiazolyl, benzotriazolyl, benzofuroxanyl, quinolinyl, isoquinolinyl, cinnolinyl, quinazolinyl, quinoxalinyl or phthalazinyl. Examples of particularly preferred compounds of the general formula I are compiled in Table 1 below.

TABLE 1

Compounds of the structure Ia

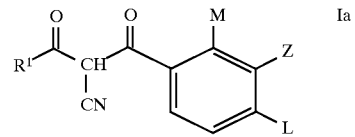

| No. | R¹ | L | M | Z |
|---|---|---|---|---|
| 1.1 | cyclopropyl | SO₂CH₃ | Cl | 2-thienyl |
| 1.2 | cyclopropyl | SO₂CH₃ | Cl | 3-thienyl |
| 1.3 | cyclopropyl | SO₂CH₃ | Cl | 2-furyl |
| 1.4 | cyclopropyl | SO₂CH₃ | Cl | 3-furyl |
| 1.5 | cyclopropyl | SO₂CH₃ | Cl | cyclopropyl |
| 1.6 | cyclopropyl | SO₂CH₃ | Cl | 3-methylisoxazol-5-yl |
| 1.7 | cyclopropyl | SO₂CH₃ | Cl | 5-thiazolyl |
| 1.8 | cyclopropyl | SO₂CH₃ | Cl | 4-thiazolyl |
| 1.9 | cyclopropyl | SO₂CH₃ | Cl | 2-thiazolyl |
| 1.10 | cyclopropyl | SO₂CH₃ | Cl | 3-methylisothiazol-5-yl |
| 1.11 | cyclopropyl | SO₂CH₃ | Cl | 3-isoxazolyl |
| 1.12 | cyclopropyl | SO₂CH₃ | Cl | 5-phenylthiazol-2-yl |
| 1.13 | cyclopropyl | SO₂CH₃ | Cl | 2-pyridyl |
| 1.14 | cyclopropyl | SO₂CH₃ | Cl | 3-pyridyl |
| 1.15 | cyclopropyl | SO₂CH₃ | Cl | 4-pyridyl |
| 1.16 | cyclopropyl | SO₂CH₃ | Cl | 1-methyl-2-pyrrolyl |
| 1.17 | cyclopropyl | SO₂CH₃ | Cl | 1-methyl-1,2,4-triazol-5-yl |
| 1.18 | cyclopropyl | SO₂CH₃ | Cl | 2-benzothiazolyl |
| 1.19 | cyclopropyl | SO₂CH₃ | Cl | 2-quinolinyl |
| 1.20 | cyclopropyl | SO₂CH₃ | Cl | 1-methylbenzimidazol-2-yl |
| 1.21 | cyclopropyl | SO₂CH₃ | Cl | 2-oxazolyl |
| 1.22 | cyclopropyl | SO₂CH₃ | Cl | 1-phenylpyrazol-5-yl |
| 1.23 | cyclopropyl | SO₂CH₃ | Cl | 5-oxazolyl |
| 1.24 | cyclopropyl | SO₂CH₃ | Cl | 1-methylpyrazol-3-yl |
| 1.25 | cyclopropyl | SO₂CH₃ | Cl | 1-methylpyrazol-5-yl |
| 1.26 | cyclopropyl | SO₂CH₃ | Cl | 1,3-dimethylpyrazol-3-yl |
| 1.27 | cyclopropyl | SO₂CH₃ | Cl | 1-phenylpyrazol-3-yl |
| 1.28 | cyclopropyl | SO₂CH₃ | Cl | 1,4-dimethylpyrazol-5-yl |
| 1.29 | cyclopropyl | SO₂CH₃ | Cl | 1,3-dimethylpyrazol-4-yl |
| 1.30 | cyclopropyl | SO₂CH₃ | Cl | 1,5-dimethylpyrazol-4-yl |
| 1.31 | cyclopropyl | SO₂CH₃ | Cl | 1-methylpyrazol-4-yl |
| 1.32 | cyclopropyl | SO₂CH₃ | Cl | 1,3-dimethylpyrazol-5-yl |
| 1.33 | cyclopropyl | SO₂CH₃ | Cl | 4-methyloxazol-2-yl |
| 1.34 | cyclopropyl | SO₂CH₃ | Cl | 5-methylthiothiazol-2-yl |
| 1.35 | cyclopropyl | SO₂CH₃ | Cl | 4-methoxy-1-methylpyrazol-5-yl |
| 1.36 | cyclopropyl | SO₂CH₃ | Cl | 3-cyclopropyl-isoxazol-5-yl |
| 1.37 | cyclopropyl | SO₂CH₃ | Cl | 3-isopropylisoxazol-5-yl |
| 1.38 | cyclopropyl | SO₂CH₃ | Cl | (3-methylphenyl)thiazol-2-yl |
| 1.39 | cyclopropyl | SO₂CH₃ | Cl | 5-methylthiazol-2-yl |
| 1.40 | cyclopropyl | SO₂CH₃ | Cl | 4-bromo-2-thienyl |
| 1.41 | cyclopropyl | SO₂CH₃ | Cl | 5-methyl-2-thienyl |
| 1.42 | cyclopropyl | SO₂CH₃ | Cl | 4-methyl-2-thienyl |
| 1.43 | cyclopropyl | SO₂CH₃ | Cl | 4-methylthiazol-2-yl |
| 1.44 | cyclopropyl | SO₂CH₃ | Cl | 4-chlorothiazol-2-yl |

TABLE 1-continued

Compounds of the structure Ia

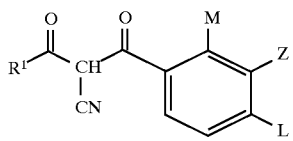

| No. | R¹ | L | M | Z |
|---|---|---|---|---|
| 1.45 | cyclopropyl | SO₂CH₃ | Cl | 4,5-dimethylthiazol-2-yl |
| 1.46 | cyclopropyl | SO₂CH₃ | Cl | 4-phenylthiazol-2-yl |
| 1.47 | cyclopropyl | SO₂CH₃ | Cl | 2-methoxythiazol-5-yl |
| 1.48 | cyclopropyl | SO₂CH₃ | Cl | 4-methyl-2-pyridyl |
| 1.49 | cyclopropyl | SO₂CH₃ | Cl | 6-(2-methoxyethyl)-2-pyridyl |
| 1.50 | cyclopropyl | SO₂CH₃ | Cl | 6-methylthio-2-pyridyl |
| 1.51 | cyclopropyl | SO₂CH₃ | Cl | 6-methoxy-3-pyridyl |
| 1.52 | cyclopropyl | SO₂CH₃ | Cl | 6-methoxy-2-pyridyl |
| 1.53 | cyclopropyl | SO₂CH₃ | Cl | 6-methyl-2-pyridyl |
| 1.54 | cyclopropyl | SO₂CH₃ | Cl | 6-(2,2,2-trifluoroethoxy)-2-pyridyl |
| 1.55 | cyclopropyl | SO₂CH₃ | Cl | 6-(2,2,2-trifluoroethoxy)-3-pyridyl |
| 1.56 | cyclopropyl | SO₂CH₃ | Cl | 5-pyrimidinyl |
| 1.57 | cyclopropyl | SO₂CH₃ | Cl | 6-dimethylamino-3-pyridyl |
| 1.58 | cyclopropyl | SO₂CH₃ | Cl | 1,2,4-thiadiazol-5-yl |
| 1.59 | cyclopropyl | SO₂CH₃ | Cl | 3-ethoxycarbonyl-1-methyl-pyrazol-5-yl |
| 1.60 | cyclopropyl | SO₂CH₃ | Cl | 2-methylthiopyrimidin-5-yl |
| 1.61 | cyclopropyl | SO₂CH₃ | Cl | 2-pyrimidinyl |
| 1.62 | cyclopropyl | SO₂CH₃ | Cl | 2-methylthiopyrimidin-4-yl |
| 1.63 | cyclopropyl | SO₂CH₃ | Cl | 5-methylthio-1,3,4-thiadiazol-2-yl |
| 1.64 | cyclopropyl | SO₂CH₃ | Cl | 4,5-dihydrothiazol-2-yl |
| 1.65 | cyclopropyl | SO₂CH₃ | Cl | 5-methyloxazol-2-yl |
| 1.66 | cyclopropyl | SO₂CH₃ | Cl | 5-phenyloxazol-2-yl |
| 1.67 | cyclopropyl | SO₂CH₃ | Cl | 2-methyloxazol-5-yl |
| 1.68 | cyclopropyl | SO₂CH₃ | Cl | 2-phenyloxazol-5-yl |
| 1.69 | cyclopropyl | SO₂CH₃ | Cl | 2-methyl-1,3,4-oxadiazol-5-yl |
| 1.70 | cyclopropyl | SO₂CH₃ | Cl | 2-phenyl-1,3,4-oxadiazol-5-yl |
| 1.71 | cyclopropyl | SO₂CH₃ | Cl | 5-trifluoromethyl-1,2,4-oxadiazol-3-yl |
| 1.72 | cyclopropyl | SO₂CH₃ | Cl | 5-methyl-1,2,4-oxadiazol-3-yl |
| 1.73 | cyclopropyl | SO₂CH₃ | Cl | 5-phenyl-1,2,4-oxadiazol-3-yl |
| 1.74 | cyclopropyl | SO₂CH₃ | Cl | 5-phenyl-isoxazol-3-yl |
| 1.75 | cyclopropyl | SO₂CH₃ | Cl | 1-(4-chlorophenyl)-1,2,4-triazol-2-yl |
| 1.76 | cyclopropyl | SO₂CH₃ | Cl | 5-cyano-4,5-dihydroisoxazol-3-yl |
| 1.77 | cyclopropyl | SO₂CH₃ | Cl | 5,6-dihydro-4H-1,3-thiazin-2-yl |
| 1.78 | cyclopropyl | SO₂CH₃ | Cl | 1,3-dithiolan-2-yl |
| 1.79 | cyclopropyl | SO₂CH₃ | Cl | 1,3-dioxolan-2-yl |
| 1.80 | cyclopropyl | SO₂CH₃ | Cl | 1,3-dithian-2-yl |
| 1.81 | cyclopropyl | SO₂CH₃ | Cl | 1,3-dioxan-2-yl |
| 1.82 | cyclopropyl | SO₂CH₃ | Cl | 1,3-oxathiolan-2-yl |
| 1.83 | cyclopropyl | SO₂CH₃ | Cl | 1,2,4-triazol-1-yl |
| 1.84 | cyclopropyl | SO₂CH₃ | Cl | 3-methyl-1,2,4-thiadiazol-5-yl |
| 1.85 | cyclopropyl | SO₂CH₃ | Cl | 1,2,4-thiadiazol-5-yl |
| 1.86 | cyclopropyl | SO₂CH₃ | Cl | thiazolin-4,5-dion-2-yl |
| 1.87 | cyclopropyl | SO₂CH₃ | Cl | 3-oxo-3-H-1,2,4-dithiazol-5-yl |
| 1.88 | cyclopropyl | SO₂CH₃ | Cl | 2-oxo-2-H-1,3,4-dithiazol-5-yl |
| 1.89 | tert-butyl | SO₂CH₃ | Cl | 3-thienyl |
| 1.90 | tert-butyl | SO₂CH₃ | Cl | 2-furyl |
| 1.91 | tert-butyl | SO₂CH₃ | Cl | 3-furyl |
| 1.92 | tert-butyl | SO₂CH₃ | Cl | 3-methylisoxazol-5-yl |
| 1.93 | tert-butyl | SO₂CH₃ | Cl | 5-thiazolyl |
| 1.94 | tert-butyl | SO₂CH₃ | Cl | 4-thiazolyl |
| 1.95 | tert-butyl | SO₂CH₃ | Cl | 2-thiazolyl |
| 1.96 | tert-butyl | SO₂CH₃ | Cl | 3-isoxazolyl |
| 1.97 | tert-butyl | SO₂CH₃ | Cl | 2-pyridyl |
| 1.98 | tert-butyl | SO₂CH₃ | Cl | 3-pyridyl |
| 1.99 | tert-butyl | SO₂CH₃ | Cl | 4-pyridyl |
| 1.100 | tert-butyl | SO₂CH₃ | Cl | 2-benzothiazolyl |
| 1.101 | tert-butyl | SO₂CH₃ | Cl | 2-quinolinyl |
| 1.102 | tert-butyl | SO₂CH₃ | Cl | 4-methyloxazol-2-yl |
| 1.103 | tert-butyl | SO₂CH₃ | Cl | 5-pyrimidinyl |

TABLE 1-continued

Compounds of the structure Ia

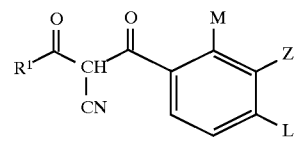

| No. | R¹ | L | M | Z |
|---|---|---|---|---|
| 1.104 | cyclopropyl | SO₂CH₃ | CH₃ | 3-thienyl |
| 1.105 | cyclopropyl | SO₂CH₃ | CH₃ | 2-furyl |
| 1.106 | cyclopropyl | SO₂CH₃ | CH₃ | 3-furyl |
| 1.107 | cyclopropyl | SO₂CH₃ | CH₃ | 3-methylisoxazol-5-yl |
| 1.108 | cyclopropyl | SO₂CH₃ | CH₃ | 5-thiazolyl |
| 1.109 | cyclopropyl | SO₂CH₃ | CH₃ | 4-thiazolyl |
| 1.110 | cyclopropyl | SO₂CH₃ | CH₃ | 2-thiazolyl |
| 1.111 | cyclopropyl | SO₂CH₃ | CH₃ | 3-isoxazolyl |
| 1.112 | cyclopropyl | SO₂CH₃ | CH₃ | 2-pyridyl |
| 1.113 | cyclopropyl | SO₂CH₃ | CH₃ | 3-pyridyl |
| 1.114 | cyclopropyl | SO₂CH₃ | CH₃ | 4-pyridyl |
| 1.115 | cyclopropyl | SO₂CH₃ | CH₃ | 2-benzothiazolyl |
| 1.116 | cyclopropyl | SO₂CH₃ | CH₃ | 2-quinolinyl |
| 1.117 | cyclopropyl | SO₂CH₃ | CH₃ | 2-methyloxazol-2-yl |
| 1.118 | cyclopropyl | SO₂CH₃ | CH₃ | 5-pyrimidinyl |

The compounds I and their agriculturally useful salts are suitable as herbicides, both as isomer mixtures and in the form of the pure isomers. The herbicidal compositions comprising I effect very good control of vegetation on uncultivated land, in particular at high application rates. In crops such as wheat, rice, corn, soya and cotton, they act against broad-leaf weeds and grass weeds while leaving the crop plants essentially unharmed. This effect is particularly pronounced at low application rates.

Taking into consideration the versatility of the application methods, the compounds I, or the compositions comprising them, can also be employed in a large number of crop plants for eliminating undesirable plants. Examples of suitable crops are the following:

*Allium cepa, Ananas comosus, Arachis hypogaea, Asparagus officinalis, Beta vulgaris ssp. altissima, Beta vulgaris ssp. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

In addition, the compounds I can also be used in crops which have been rendered tolerant to the action of herbicides by means of breeding including genetic engineering methods.

The herbicidal compositions, or the active ingredients, can be applied pre- or post-emergence. If the active ingredients are less well tolerated by certain crop plants, application techniques can be used in which the herbicidal compositions are sprayed, with the aid of the spraying equipment, in such a way that the leaves of the sensitive crop plants come into as little contact as possible with the active ingredients, while they reach the leaves of undesirable plants which grow underneath, or the naked soil surface (post-directed, lay-by).

The compounds I, or the herbicidal compositions comprising them, can be applied, for example, in the form of ready-to-spray aqueous solutions, powders, suspensions, even highly-concentrated aqueous, oily or other suspensions or dispersions, emulsions, oil dispersions, pastes, dusts, spreading materials or granules, by means of spraying, atomizing, dusting, scattering or pouring. The use forms depend on the intended purposes; in any case, they should guarantee the finest possible distribution of the active ingredients according to the invention.

Suitable inert auxiliaries are mineral oil fractions of medium to high boiling point, such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, adhesive, dispersant or emulsifier. Alternatively, concentrates may be prepared which are composed of active ingredient, wetting agent, adhesive, dispersant or emulsifier and, if desired, solvent or oil, and which are suitable for dilution with water.

Suitable surfactants are the alkali metal, alkaline earth metal and ammonium salts of aromatic sulfonic acids, eg. lignosulfonic acid, phenolsulfonic acid, naphthalenesulfonic acid and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensation products of sulfonated naphthalene and derivatives thereof with formaldehyde, condensation products of naphthalene or naphthalenesulfonic acids with phenol and formaldehyde, polyoxyethylene octyl phenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, spreading materials and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths, such as silicic acids, silica gels, silicates, talc, kaolin, limestone, lime, chalk, bole, loess, clay, dolomite, diatomaceous earth, calcium sulfate, magnesium sulfate, magnesium oxide, ground synthetic substances, fertilizers, such as ammonium sulfate, ammonium phosphate, ammonium nitrate, ureas and products of vegetable origin, such as cereal meal, tree bark meal, wood meal and nutshell meal, cellulose powder, or other solid carriers.

The concentrations of the active ingredients I in the ready-to-use preparations can be varied within wide ranges. In general, the formulations comprise from 0.001 to 98% by weight, preferably 0.01 to 95% by weight, of active ingredient. The active ingredients are employed in a purity of from 90% to 100%, preferably 95% to 100% (according to NMR spectrum).

The compounds I according to the invention can be formulated for example as follows:

I 20 parts by weight of compound No. 1.23 are dissolved in a mixture which is composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzene sulfonate and 5 parts by weight of the adduct of 40 mol of ethylene oxide to 1 mol of castor oil. Pouring the solution into 100000 parts by weight of water and finely dispersing it therein gives an aqueous dispersion which comprises 0.02% by weight of the active ingredient.

II 20 parts by weight of compound No. 1.23 are dissolved in a mixture which is composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100000 parts by weight of water and finely dispersing it therein gives an aqueous dispersion which comprises 0.02% by weight of the active ingredient.

III 20 parts by weight of active ingredient No. 1.23 are dissolved in a mixture which is composed of 25 parts by weight of cyclohexanone, 65 parts by weight of a mineral oil fraction of boiling point 210° to 280° C. and 10 parts by weight of the adduct of 40 mol of ethylene oxide to 1 mol of castor oil. Pouring the solution into 100000 parts by weight of water and finely dispersing it therein gives an aqueous dispersion which comprises 0.02% by weight of the active ingredient.

IV 20 parts by weight of active ingredient No. 1.23 are thoroughly mixed with 3 parts by weight of sodium diisobutylnaphthalene-α-sulfonate, 17 parts by weight of sodium lignosulfonate from a sulfite waste liquor and 60 parts by weight of pulverulent silica gel, and the mixture is ground in a hammer mill. Finely dispersing the mixture in 20000 parts by weight of water gives a spray mixture which comprises 0.1% by weight of the active ingredient.

V 3 parts by weight of active ingredient No. 1.23 are mixed with 97 parts by weight of finely divided kaolin. This gives a dust which comprises 3% by weight of the active ingredient.

VI 20 parts by weight of active ingredient No. 1.23 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of compound No. 1.23 is dissolved in a mixture which is composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of compound No. 1.23 is dissolved in a mixture which is composed of 80 parts by weight of cyclohexanone and 20 parts by weight of Emulphor EL. This gives a stable emulsion concentrate.

To broaden the spectrum of action and to achieve synergistic effects, the phenyldiketone derivatives I can be mixed with a large number of representatives of other groups of herbicidal or growth-regulating active ingredients and this mixture then applied. Suitable components in mixtures are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which have attached to them in the 2-position for example a carboxyl or carbimino group, quinolinecarboxylic acid derivatives, imidazolinones, sulfonamides, sulfonylureas, aryloxy- or heteroaryloxyphenoxypropionic acids and their salts, esters and amides, and others.

It may additionally be useful to apply the compounds I, on their own or in combination with other herbicides, together with further crop protection agents, for example with pesticides or agents for controlling phytopathogenic fungi or bacteria. Also of interest is the miscibility with mineral salt solutions, which are employed for eliminating nutritional and trace element deficiencies. Non-phytotoxic oils and oil concentrates may also be added.

Depending on the intended purpose, the season, the target plants and the growth stage, the application rates of active ingredient are from 0.001 to 3.0, preferably 0.01 to 1.0, kg of active ingredient (a.i.) per ha.

Examples

The herbicidal action of the phenyldiketone derivatives of the formula I was demonstrated by greenhouse experiments:

Plastic flowerpots containing loamy sand and approximately 3.0% of humus as substrate were used as culture containers. The seeds of the test plants were sown separately, according to species.

For the pre-emergence treatment, the active ingredients which were suspended or emulsified in water were applied directly after sowing, using finely dispersing nozzles. The containers were irrigated lightly to promote germination and growth, and subsequently covered with transparent plastic hoods until the plants had rooted. This hood causes uniform germination of the test plants, unless this has been adversely affected by the active ingredients.

For post-emergence treatment, the test plants were first grown to a plant height of 3 to 15 cm, depending on the growth form, and only then treated with the active ingredients which were suspended or emulsified in water. The test plants were either sown directly and grown on in the same containers, or first grown separately as seedlings and transplanted to the test containers a few days prior to treatment. Depending on the species, the plants were kept at 10°–25° C. or 20°–35° C. The test period extended over 2–4 weeks. During this time, the plants were tended, and their response to the individual treatments was evaluated.

Assessment was carried out using a scale from 0 to 100. 100 means that no plants emerge, or that at least the aerial parts are completely destroyed, and 0 denotes no damage, or normal growth.

Preparation Examples

A) Preparation of the Starting Materials

1. Methyl 2-chloro-3-formyl-4-methylsulfonylbenzoate a. A solution of 157 g (2 mol) of acetyl chloride in 420 mol of 1,2-dichloroethane was added dropwise at 15°–20° C. to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was subsequently added dropwise. After stirring of the reaction mixture had been continued for 12 hours, it was poured into a mixture of 3 l of ice and 1 l of concentrated HCl. The mixture was extracted using methylene chloride, and the organic phase was washed with water, dried using sodium sulfate and concentrated. The residue was distilled in vacuo.

This gave 256 g (60% of theory) of 2-chloro-3-methyl-4-methylthioacetophenone, m.p.: 46° C.

b. 163 g (0.76 mol) of 2-chloro-3-methyl-4-methylthioacetophenone were dissolved in 1.5 l of glacial acetic acid, 18.6 g of sodium tungstate were added, and 173.3 g of 30% strength hydrogen peroxide solution were added dropwise with cooling. Stirring was continued for 2 days and the mixture was subsequently diluted with water. The solid which had precipitated was filtered off with suction, washed with water and dried.

This gave 164 g (88% of theory) of 2-chloro-3-methyl-4-methylsulfonylacetophenone, m.p.: 110°–111° C.

c. 82 g (0.33 mol) of 2-chloro-3-methyl-4-methylsulfonylacetophenone were dissolved in 700 ml of dioxane, and 1 l of a 12.5% strength sodium hypochlorite solution was added at room temperature. Stirring was subsequently continued at 80° C. for 1 hour. After cooling, two phases formed, of which the bottom phase was diluted with water and rendered weakly acidic. The solid which had precipitated was washed with water and dried.

This gave 60 g (73% of theory) of 2-chloro-3-methyl-4-methylsulfonylbenzoic acid, m.p.: 230°–231° C.

d. 100 g (0.4 mol) of 2-chloro-3-methyl-4-methylsulfonylbenzoic acid were dissolved in 1 l of methanol, and HCl was passed in for 5 hours at reflux temperature. The mixture was subsequently concentrated.

This gave 88.5 g (84% of theory) of methyl 2-chloro-3-methyl-4-methylsulfonylbenzoate, m.p.: 107°–108° C.

e. 82 g (0.31 mol) of 2-chloro-3-methyl-4-methylsulfonylbenzoate were dissolved in 2 l of tetrachloromethane, and 56 g (0.31 mol) of N-bromosuccinimide were added, a little at a time and with exposure to light. The reaction mixture was filtered, the filtrate was concentrated, and the residue was taken up in 200 ml of methyl tert-butyl ether. The solution was treated with petroleum ether, and the solid which had precipitated was filtered off with suction and dried.

This gave 74.5 g (70% of theory) of methyl 3-bromomethyl-2-chloro-4-methylsulfonylbenzoate, m.p.: 74°–75° C.

f. A solution of 41 g (0.12 mol) of methyl 3-bromomethyl-2-chloro-4-methylsulfonylbenzoate in 250 ml of acetonitrile was treated with 42.1 g (0.36 mol) of N-methylmorpholine N-oxide. Stirring of the batch was continued at room temperature for 12 hours, the mixture was subsequently concentrated, and the residue was taken up in ethyl acetate. The solution was extracted with water, dried using sodium sulfate and concentrated.

This gave 31.2 g (94% of theory) of methyl 2-chloro-3-formyl-4-methylsulfonylbenzoate, m.p.: 98°–105° C.

2. Methyl 2-chloro-4-methylsulfonyl-3-(trifluoromethylsulfonyl)oxybenzoate a. 101 g (0.41 mol) of 2-chloro-3-hydroxy-4-methylsulfonylbenzoic acid were dissolved in 1.3 l of methanol, and HCl was passed in for 4 hours under reflux. The solution was concentrated, and the residue was taken up in dichloromethane and extracted using $K_2CO_3$ solution. The aqueous phase was brought to pH 7 using dilute hydrochloric acid and washed using dichloromethane. It was subsequently acidified to pH 1 and the product was extracted using dichloromethane.

This gave 76.2 g (71% of theory) of methyl 2-chloro-3-hydroxy-4-methylsulfonylbenzoate.

b. 89 g (0.32 mol) of trifluoromethanesulfonic anhydride were added at –20° C. to a solution of 76 g (0.29 mol) of methyl 2-chloro-3-hydroxy-4-methylsulfonylbenzoate and 68 g of pyridine in 700 ml of dichloromethane. Stirring of the solution was continued for 12 hours at room temperature, and the mixture was diluted with dichloromethane and extracted using water. The organic phase was dried over magnesium sulfate and concentrated.

This gave 94 g (82% of theory) of methyl 2-chloro-4-methylsulfonyl-3-(trifluoromethylsulfonyl)oxybenzoate, m.p.: 69° C.

B) Preparation of the Intermediates

1. Methyl 3-(3-isopropylisoxazol-5-yl)-4-methylsulfonylbenzoate a. 10 g (102 mmol) of (trimethylsilyl)acetylene and 180 mg of copper(I) iodide were added to 30 g (102 mmol) of methyl 3-bromo-4-methylsulfonylbenzoate, 90 mg of palladium dichloride and 240 mg of triphenylphosphine in 200 ml of diethylamine and 60 ml of dimethylformamide, and the mixture was stirred at 40° C. for 4.5 hours. Stirring was subsequently continued at room temperature for 12 hours. The reaction mixture was filtered, the filtrate was concentrated, and the residue was chromatographed over silica gel using toluene as the eluent.

This gave 17.3 g (55% of theory) of methyl 4-methylsulfonyl-3-(trimethylsilyl)ethynylbenzoate as an oil.

b. 25 g of methyl 4-methylsulfonyl-3-(trimethylsilyl) ethynylbenzoate were stirred at room temperature for 18 hours with 100 ml of methanol and 0.9 g of potassium carbonate. Solids were subsequently filtered off with suction, and the filtrate was concentrated and extracted using ethyl acetate/water. The organic phase was dried over sodium sulfate and concentrated.

This gave 15 g (79% of theory) of methyl 4-methylsulfonyl-3-ethynylbenzoate, m.p.: 95°–98° C.

c. 13.5 g (57 mmol) of methyl 4-methylsulfonyl-3-ethynylbenzoate were dissolved in 50 ml of dichloromethane, 5.2 g (60 mmol) of isobutyraldehyde oxime were added, and 41 g of a 12.5% strength sodium hypochlorite solution were added dropwise. Stirring was subsequently continued for 24 hours at room temperature. The reaction batch was subsequently extracted using dichloromethane/water, the organic phase was concentrated, and the residue was chromatographed over silica gel using toluene/ethyl acetate as the eluent.

This gave 8.8 g (48% of theory) of methyl 3-(3-isopropylisoxazol-5-yl)-4-methylsulfonylbenzoate, m.p.: 102°–104° C.

2. Methyl 2-chloro-3-(isoxazol-3-yl)-4-methylsulfonylbenzoate a. 15 g (54 mmol) of methyl 2-chloro-3-formyl-4-methylsulfonylbenzoate (Ex. A.1.) and 4.2 g (60 mmol) of hydroxylamine hydrochloride were stirred with 300 ml of methanol, and a solution of 3.18 g (30 mmol) of sodium carbonate in 80 ml of water was added dropwise. The reaction mixture was stirred overnight at room temperature, the methanol was subsequently distilled off, and the batch was extracted using ether/water. The ether phase was dried using sodium sulfate and concentrated.

This gave 14.4 g (91% of theory) of methyl 2-chloro-3-hydroxyiminomethyl-4-methylsulfonylbenzoate, m.p.: 126°–128° C.

b. 5.3 g (18 mmol) of methyl 2-chloro-3-hydroxyiminomethyl-4-methylsulfonylbenzoate were dissolved in 50 ml of dichloromethane, and acetylene was passed in for 30 minutes at 0°–5° C. A spatula-tip full of sodium acetate was subsequently added, and 15 ml of a 10% strength sodium hypochlorite solution was added dropwise at 10° C. while passing in more acetylene. After the addition had ended, acetylene was passed in for a further 15 minutes at 10° C., and stirring was subsequently continued for 12 hours. Thereupon, the phases were separated, the organic phase was washed with water, dried using sodium sulfate and concentrated.

This gave 4.8 g (84% of theory) of methyl 2-chloro-3-(isoxazol-3-yl)-4-methylsulfonylbenzoate, m.p.: 145°–147° C.

3. Methyl 2-chloro-3-(thiazol-2-yl)-4-methylsulfonylbenzoate

In an autoclave, 33 g (88 mmol) of 2-(tributylstannyl) thiazole, 17.5 g (44 mmol) of methyl 2-chloro-4-methylsulfonyl-3-(trifluoromethylsulfonyl)oxybenzoate (Ex. A.2.), 5.8 g of lithium chloride, 1 g of tetrakis (triphenylphosphine)palladium(0), a spatula-tip full of 2,6-di-tert-butyl-4-methylphenol and 200 ml of 1,4-dioxane were stirred at 140° C. for 3 hours under inherent pressure. After cooling, the reaction mixture was filtered through a layer of silica gel, washed using methyl tert-butyl ether and concentrated. The residue was chromatographed over silica gel using toluene/ethyl acetate as the eluent.

This gave 9.1 g (62.6% of theory) of methyl 2-chloro-3-(thiazol-2-yl)-4-methylsulfonylbenzoate, m.p.: 135°–138° C.

4. Methyl 2-chloro-3-(oxazol-2-yl)-4-methylsulfonylbenzoate 25 g (0.09 mol) of methyl 2-chloro-3-formyl-4-methylsulfonylbenzoate (Ex. A.1.), 17.6 g (0.09 mol) of tosylmethylene isocyanide, 6.2 g (0.045 mol) of finely pulverulent potassium carbonate and 450 ml of methanol were stirred at reflux temperature for 5 hours. The solvent was subsequently stripped off, the residue was taken up in ethyl acetate, and the mixture was extracted using water. The ethyl acetate phase was dried using sodium sulfate and concentrated.

This gave 24.7 g (87% of theory) of methyl 2-chloro-3-(oxazol-2-yl)-4-methylsulfonylbenzoate, $^1$H NMR (CDCl$_3$) δ: 8.24 (d,1H), 8.15 (s,1H), 8.01 (d,1H), 7.40 (s,1H), 4.0 (s,3H), 2.96 (s,3H)

The intermediates listed in the table below were obtained analogously.

TABLE 2

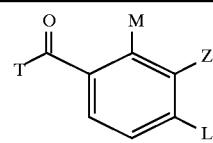

IIIa

| No. | T | L | M | Z | Physical data M.p. [°C.] or $^1$H NMR |
|---|---|---|---|---|---|
| 2.1 | methoxy | —SO$_2$Me | Cl | 3-furyl | $^1$H NMR (CDCl$_3$) δ: 8.24 (d,1H), 7.82 (d,1H), 7.64 (m,2H), 6.55 (s,1H) 3.99 (s,3H), 2.80 (s,3H) |
| 2.2 | methoxy | —SO$_2$Me | H | 2-thiazolyl | 95–98 |
| 2.3 | ethoxy | —SO$_2$Et | Cl | 2-thiazolyl | $^1$H NMR (CDCl$_3$) δ: 8.18 (d,1H), 7.97 (m,2H), 7.71 (d,1H)), 4.47 (q,2H) 3.36 (q,2H), 1.42 (t,3H) 1.24 (t,3H) |
| 2.4 | OH | —SO$_2$CH$_3$ | Cl | 2-thiazolyl | 288–290 |
| 2.5 | OH | —SO$_2$CH$_3$ | Cl | 2-thienyl | 177–180 |
| 2.6 | OH | —SO$_2$CH$_3$ | CH$_3$ | 2-thienyl | 175–178 |
| 2.7 | OH | —SO$_2$CH$_3$ | CH$_3$ | 2-furyl | 167–171 |
| 2.8 | methoxy | —SO$_2$CH$_3$ | CH$_3$ | 2-thienyl | 91–95 |
| 2.9 | OH | —SO$_2$CH$_3$ | H | 2-furyl | 219–223 |
| 2.10 | methoxy | —SO$_2$CH$_3$ | CH$_3$ | 2-furyl | 103–106 |
| 2.11 | OH | —SO$_2$CH$_3$ | H | 2-thienyl | 222–224 |
| 2.12 | methoxy | —SO$_2$CH$_3$ | Cl | 3-isoxazolyl | $^1$H NMR (CDCl$_3$): 8.62 (1H); 8.18 (1H); 8.00 (1H); 6.58 (1H); 3.98 (3H); 3.22 (3H) |
| 2.13 | methoxy | —SO$_2$CH$_3$ | Cl | 5-phenyl-oxazol-2-yl | 1.15–118 |
| 2.14 | methoxy | —SO$_2$CH$_3$ | Cl | 5-oxazolyl | $^1$H NMR (CDCl$_3$): 8.76 (1H); 8.22 (1H); 8.10 (1H); 7.63 (1H) 4.04 (3H); 3.08 (3H) |
| 2.15 | methoxy | —SO$_2$CH$_3$ | Cl | 5-cyclopropyl-isoxazolylpropyl- | $^1$H NMR (CDCl$_3$): 8.20 (1H); 7.95 (1H); 6.12 (1H); 3.98 (3H); 3.22 (3H); 2.15 (1H); 1.03–1.09 (4H) |
| 2.16 | methoxy | —SO$_2$CH$_3$ | Cl | 4,5-dihydro-isoxazol-3-yl | $^1$H NMR (CDCl$_3$): 8.12 (1H); 7.98 (1H); 4.60 (2H); 3.98 (3H); 3.42 (2H); 3.25 (3H) |
| 2.17 | methoxy | —SO$_2$CH$_3$ | Cl | 5-methyl-1,2,4-oxadiazol-3-yl | 102–105 |
| 2.18 | methoxy | —SO$_2$CH$_3$ | Cl | 4,5-dihydro-oxazol-2-yl | $^1$H NMR (CDCl$_3$): 8.08 (1H); 7.98 (1H); 4.57 (2H); 4.12 (2H); 3.98 (3H); 3.29 (3H) |
| 2.19 | OH | —SO$_2$CH$_3$ | Cl | 3-furyl | $^1$H NMR (CDCl$_3$): 8.29 (1H); 8.02 (1H); 7.67 (2H); 6.59 (1H); 2.83 (3H) |
| 2.20 | methoxy | —SO$_2$CH$_3$ | Cl | 3-thienyl | $^1$H NMR (CDCl$_3$): 8.23 (1H); 7.84 (1H); 7.49 (2H); 7.13 (1H); 3.98 (3H); 2.62 (3H) |
| 2.21 | OH | —SO$_2$CH$_3$ | H | 3-furyl | 200–202 |
| 2.22 | OH | —SO$_2$CH$_3$ | Cl | 5-methyl-4-phenyl-thiazol-2-yl | 200–204 |

C) Preparation of the End Products 1. 2-Cyano-3-cyclopropyl-1-[2-chloro-4-methylsulfonyl-(3-thiazol-2-yl)-phenyl]propane-1,3-dione a. 8 g (25 mmol) of methyl 2-chloro-4-methylsulfonyl-(3-thiazol-2-yl)benzoate are dissolved in 50 ml of methanol, and 1.5 g (37 mmol) of NaOH are added. The solution is stirred for 12 hours at room temperature. The reaction mixture is subsequently concentrated and the residue is taken up in water and acidified using hydrochloric acid. Pale yellow crystals form upon prolonged stirring. The solid is filtered off with suction and dried.
   This gives 6.6 g (86% of theory) of 2-chloro-4-methylsulfonyl-(3-thiazol-2-yl)benzoic acid, m.p.: 288°–290° C.

b. 6 g (19 mmol) of 2-chloro-4-methylsulfonyl-(3-thiazol-2-yl)benzoic acid are dissolved in 60 ml of toluene, one drop of dimethylformamide is added, and the mixture is treated with 3.2 g (27 mmol) of thionyl chloride. After refluxing for 4 hours, the reaction mixture is concentrated.

This gives 6.3 g (99% of theory) of 2-chloro-4-methylsulfonyl-(3-thiazol-2-yl)benzoyl chloride, m.p.: 97°–98° C.

c. A solution of 3.5 mmol of 3-cyclopropyl-3-oxo-propionitrile in 50 ml of methanol is treated with 0.15 g (6 mmol) of magnesium filings, and 2 ml of $CCl_4$ are added dropwise at 25° C. After the mixture has been stirred for 2 hours, the methanol is stripped off in vacuo and the residue is dissolved in 50 ml of acetonitrile. Then, a solution of 1.2 g (3.5 mmol) of 2-chloro-4-methylsulfonyl-(3-thiazol-2-yl)benzoyl chloride in 25 ml of acetonitrile is added dropwise at 20°–25° C. and the mixture is stirred for 16 hours at 25° C. For working-up, the acetonitrile is first stripped off in vacuo, the residue is dissolved in ethyl acetate, and the solution is washed with water and concentrated. The crude product is dissolved in dichloromethane and extracted using 5% strength potassium carbonate solution. The aqueous phase is brought to pH 5–6 using hydrochloric acid and extracted using dichloromethane. The organic phase is dried over sodium sulfate and concentrated.

This gives 0.23 g (17% of theory) of 2-cyano-3-cyclopropyl-1-[2-chloro-4-methylsulfonyl-(3-thiazol-2-yl)phenyl]propane-1,3-dione, m.p.: 162°–164° C.

The compounds listed in the table below are obtained in a similar manner:

TABLE 3

Compounds of the structure Ie

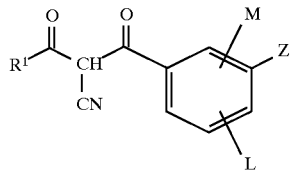

| No. | T | L | M | Z | M.p. [°C.] or $^1$H NMR |
|---|---|---|---|---|---|
| 3.1 | cyclo-propyl | —SO$_2$CH$_3$ | Cl | 3-isoxa-zolyl | $^1$H NMR(CDCl$_3$): δ 8.61 (1H), 8.29 (1H), 7.79 (1H), 6.63 (1H), 3.23 (3H), 2.38 (1H), 1.51 (2H), 1.38 (2H) |

We claim:

1. A phenyldiketone compound of the formula I

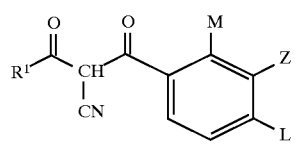

in which the substituents have the following meanings:

L and M are hydrogen, $C_1$–$C_6$-alkyl, $C_2$–$C_6$-alkenyl, $C_2$–$C_6$-alkynyl, $C_1$–$C_4$-alkoxy, it being possible for these groups to be unsubstituted or substituted by one to five halogen atoms or $C_1$–$C_4$-alkoxy, or halogen, cyano, nitro, a group —(Y)$_n$—S(O)$_m$R$^7$ or a group —(Y)$_n$—CO—R$^8$, Z is a 5- or 6-membered heterocyclic saturated or unsaturated radical which has one to three hetero atoms selected from the group consisting of oxygen, sulfur or nitrogen and which is unsubstituted or substituted by halogen, cyano, nitro, a group —CO—R$^8$, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino or phenyl which is unsubstituted or substituted by halogen, cyano, nitro, $C_1$–$C_4$-alkyl or $C_1$–$C_4$-haloalkyl or an oxo group which may also exist as a hydroxyl group in the tautomeric form, or which forms a bicyclic system with a fused phenyl ring which is unsubstituted or substituted by halogen, cyano, nitro, $C_1$–$C_4$-alkyl or $C_1$–$C_4$-haloalkyl, a fused carbocycle or a fused, second heterocycle which is unsubstituted or substituted by halogen, cyano, nitro, $C_1$–$C_4$-alkyl, di-$C_1$–$C_4$-alkylamino, $C_1$–$C_6$-alkoxy, $C_1$–$C_4$-haloalkoxy or $C_1$–$C_4$-haloalkyl, Y is O or NR$^9$, n is zero or one, m is zero, one or two, R$^7$ is $C_1$–$C_4$-alkyl, $C_1$–$C_4$-haloalkyl or NR$^9$R$^{10}$, R$^8$ is $C_1$–$C_4$-alkyl, $C_1$–$C_4$-haloalkyl, $C_1$–$C_4$-alkoxy or NR$^9$R$^{10}$, R$^9$ is hydrogen or $C_1$–$C_4$-alkyl, R$^{10}$ is $C_1$–$C_4$-alkyl, R$^1$ is cyclopropyl, 1-methylcyclopropyl, 1-methylthiocyclopropyl or tert-butyl;

or an agriculturally customary salt of the compound I.

2. A phenyldiketone compound of the formula Ia

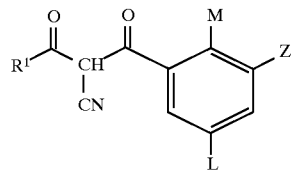

where L is $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and m is hydrogen, $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano, and R$^1$ and Z have the meanings given in claim 1.

3. A phenyldiketone compound of the formula Ib

Ib where L and M are $C_1$–$C_6$-alkyl, $C_2$–$C_6$-alkenyl, $C_2$–$C_6$-alkynyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-haloalkylthio, $C_1$–$C_4$-alkylsulfonyl, halogen, nitro or cyano and R$^1$ and Z have the meanings given in claim 1.

4. A phenyldiketone compound of the formula I as defined in claim 1, where the radicals L and M are hydrogen, methyl, methoxy, methylthio, chlorine, cyano, methylsulfonyl, nitro or trifluoromethyl.

5. A process for the preparation of the phenyldiketone compounds of the formula I as defined in claim 1, which comprises reacting compounds of the formula A2

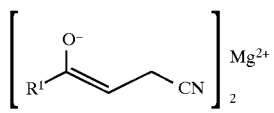

with a benzoic acid derivative of the formula III

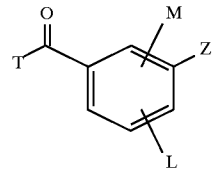

where T=halogen and L, M and Z have the meanings given in claim 1.

6. A herbicidal composition comprising at least one phenyldiketone compound of the formula I as defined in claim 1 and inert additives.

7. A method of controlling undesirable vegetation, which comprises allowing a herbicidally active amount of a phenyldiketone compound of the formula I as defined in claim 1 to act on the plants or their environment.

8. A phenyldiketone compound of the formula I as defined in claim 1, where Z is a 5- or 6-membered heteroaromatic which has one to three hetero atoms selected from the group consisting of oxygen, sulfur or nitrogen and which is unsubstituted or substituted by halogen, cyano, nitro, $C_1$–$C_4$-alkyl, $C_1$–$C_4$-haloalkyl, $C_3$–$C_8$-cycloalkyl, $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, phenyl which is unsubstituted or substituted by halogen, cyano, nitro, $C_1$–$C_4$-alkyl or $C_1$–$C_4$-haloalkyl, or is a benzo-fused 5- or 6-membered heteroaromatic ring which is unsubstituted or substituted by halogen, cyano, nitro, $C_1$–$C_4$-alkyl or $C_1$–$C_4$-haloalkyl;

and L, M and $R^1$ have the meanings given in claim 1.

* * * * *

UNITED STATES PATENT AND TRADEMARK OFFICE
CERTIFICATE OF CORRECTION

PATENT NO.: 5,846,906

DATED: December 8, 1998

INVENTOR(S): VON DEYN et al.

It is certified that error appears in the above-identified patent and that said Letters Patent is hereby corrected as shown below:

In the abstract, last line, insert --acceptable-- after "agriculturally".

Col. 28, claim 1, line 29, "customary" should be --acceptable--.

Signed and Sealed this

Twenty-third Day of March, 1999

Attest:

Q. TODD DICKINSON

Attesting Officer

Acting Commissioner of Patents and Trademarks